United States Patent [19]

Wittwer et al.

[11] Patent Number: 5,039,791

[45] Date of Patent: Aug. 13, 1991

[54] PEPTIDE FRAGMENTS OF TISSUE PLASMINOGEN ACTIVATOR

[75] Inventors: Arthur J. Wittwer, Ellisville; Michael A. Sanzo, St. Louis, both of Mo.

[73] Assignee: Monsanto Company, St. Louis, Mo.

[21] Appl. No.: 432,256

[22] Filed: Nov. 6, 1989

[51] Int. Cl.⁵ .................. C07K 7/10; A61K 37/02; A61K 37/18

[52] U.S. Cl. .................................... 530/324; 514/12

[58] Field of Search .................. 514/12; 530/324

[56] — References Cited

FOREIGN PATENT DOCUMENTS 0198322 10/1986 European Pat. Off. .

OTHER PUBLICATIONS

Ny et al., Proc. Natl. Acad. Sci. U.S.A. 81, 5355–5359 (1984).
Hajjar et al., J. Clin. Invest. 80, 1712–1719 (1987).
Barnathan et al., J. Biol. Chem. 263, 7792–7797 (1988).
Beebe, Thromb. Res. 46, 241–254 (1987).
Sakata et al., J. Biol. Chem. 263, 1960–1969 (1988).
Chmielewska et al., Biochem. J. 251, 327–332 (1988).
Van Zonnenveld et al., J. Cellular Biochem. 32, 169–178 (1986).

*Primary Examiner*—Jeffrey E. Russel
*Assistant Examiner*—Stephen Walsh
*Attorney, Agent, or Firm*—Scott J. Meyer; James W. Williams, Jr.

[57] ABSTRACT

Novel peptide fragments of tissue plasminogen activator are described which have activity for inhibiting (a) the binding of tPA to human endothelial cells, and (b) the inactivation of tPA by plasminogen activator inhibitor-1 (PAI-1). Six peptides or peptide amides with these activities have the sequences, numbered according to the native protein:

tPA (31-55),
tPA (81-105),
tPA (181-205),
tPA (301-325),
tPA (451-475, and
tPA (531-555).

It is hoped that small, synthesizeable molecules which prevent the inactivation of tPA by PAI-1 may provide a means for improving the efficacy of therapeutically administered tPA or for reducing the tendency of patients with elevated plasma PAI-1 concentrations to form fibrin clots.

1 Claim, 4 Drawing Sheets

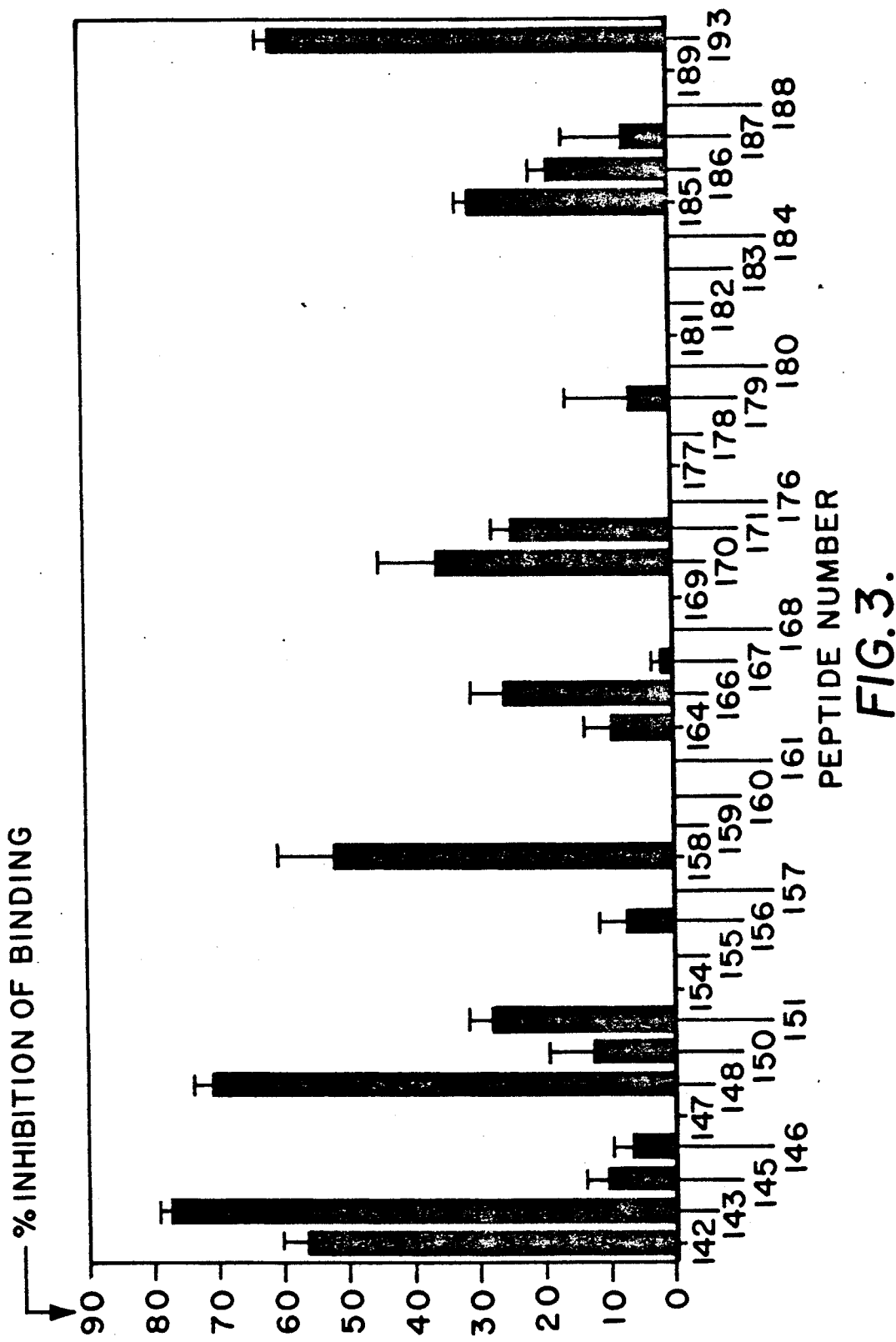

PEPTIDE FRAGMENTS OF TISSUE PLASMINOGEN ACTIVATOR

BACKGROUND OF THE INVENTION

This invention relates to novel inhibitory peptides and, more particularly, to peptides which inhibit (a) the binding of tissue plasminogen activator (tPA) to human endothelial cells and (b) the inactivation of tPA by plasminogen activator inhibitor-1 (PAI-1).

A considerable body of evidence has accumulated indicating that the ability of an individual to degrade fibrin clots is determined by the ratio of plasminogen activator inhibitor (PAI-1) to tissue plasminogen activator (tPA) found within that individual's plasma. An abnormally high ratio (i.e., an excessive concentration of PAI-1) appears to be a causative factor in a large percentage of patients with serious thromboembolic disease [Nilsson et al., Br. Med. J. 290, 1453-1456 (1985); Jorgensen and Bonnevie-Nielsen, Br. J. Haematol. 65, 175-180 (1987); and Juhan-Vague et al., Thromb. Haemost. 57, 67-72 (1987)]. Elevated levels of PAI-1 have also been associated with coronary heart disease and there is a direct correlation between plasma PAI-1 levels and the probability that a patient who has had a myocardial infarction will have a recurrence [Mehta et al., J. Am. Cell. Cardiol. 9, 263-268 (1987); and Hamsten et al., Lancet 2, 3-9 (1987)].

A number of recent reports have suggested that the release of PAI-1 by platelets at the site of clot formation may lead to localized concentrations of the inhibitor which are much higher than those found elsewhere in the plasma [Kruithof et al., Blood 70, 1645-1653 (1987); Booth et al., J. Clin. Pathol. 38, 825-830 (1985); Sprengers et al., Thromb. Haemost. 55, 325-329 (1986); and Jang et al., Circulation 79, 920-928 (1989)]. As a result, clot lysis by tPA administered therapeutically may be correspondingly less effective. Therapeutically administered tPA may also be lost due to binding to the endothelial cells lining blood vessels. These cells contain a large number of high affinity binding sites for tPA and at least a portion of the sites appear to represent membrane bound PAI-1 [Hajjar et al., J. Clin. Invest. 80, 1712-1719 (1987); Barnathan et al., J. Biol. Chem. 263, 7792-7797(1988); Beebe, Thromb. Res. 46, 241-254 (1987); and Sakata et al., J. Biol. Chem. 263, 1960-1969 (1988)].

Small, synthesizeable molecules which prevent the inactivation of tPA by PAI-1 may provide a means for either improving the efficacy of therapeutically administered tPA or for reducing the tendency of patients with elevated plasma PAI-1 concentrations to form fibrin clots.

BRIEF DESCRIPTION OF THE INVENTION

In accordance with the present invention, inhibitory peptides and peptide amides are provided which inhibit (a) the binding of tPA to human endothelial cells and (b) the inactivation of tPA by PAI-1. These inhibitory peptides and peptide amides are small, synthesizeable molecules which have amino acid sequences substantially identical to that of native tPA fragments selected from the group consisting of:
tPA(31-55),
tPA(81-105),
tPA(181-205),
tPA(301-325),
tPA(451-475) and
tPA(531-555).

Of these peptides and peptide amides, the following four are the most preferred for maintaining tPA activity:
tPA(31-55),
tPA(81-105),
tPA(301-325) and
tPA(531-555).

As used herein, the amino acid numbering system of the native tPA molecule and fragments thereof is based on the full 562 amino acid sequence including the putative signal peptide and prosequences described by Ny et al., Proc. Natl. Acad. Sci. USA 81, 5355-5359 (1984). For example, tPA(31-55) refers to the peptide fragment of native human tPA having the sequence stretch of amino acids in positions 31 to 55 inclusive. The corresponding peptide amides have an amide group instead of the free carboxy group at the carboxy terminus, i.e. —CONH$_2$. The actual sequences of these peptides are set forth in Table 1 hereinafter.

None of the foregoing peptides inhibited the binding of tPA to fibrin.

DETAILED DESCRIPTION OF THE INVENTION

Figure 1:
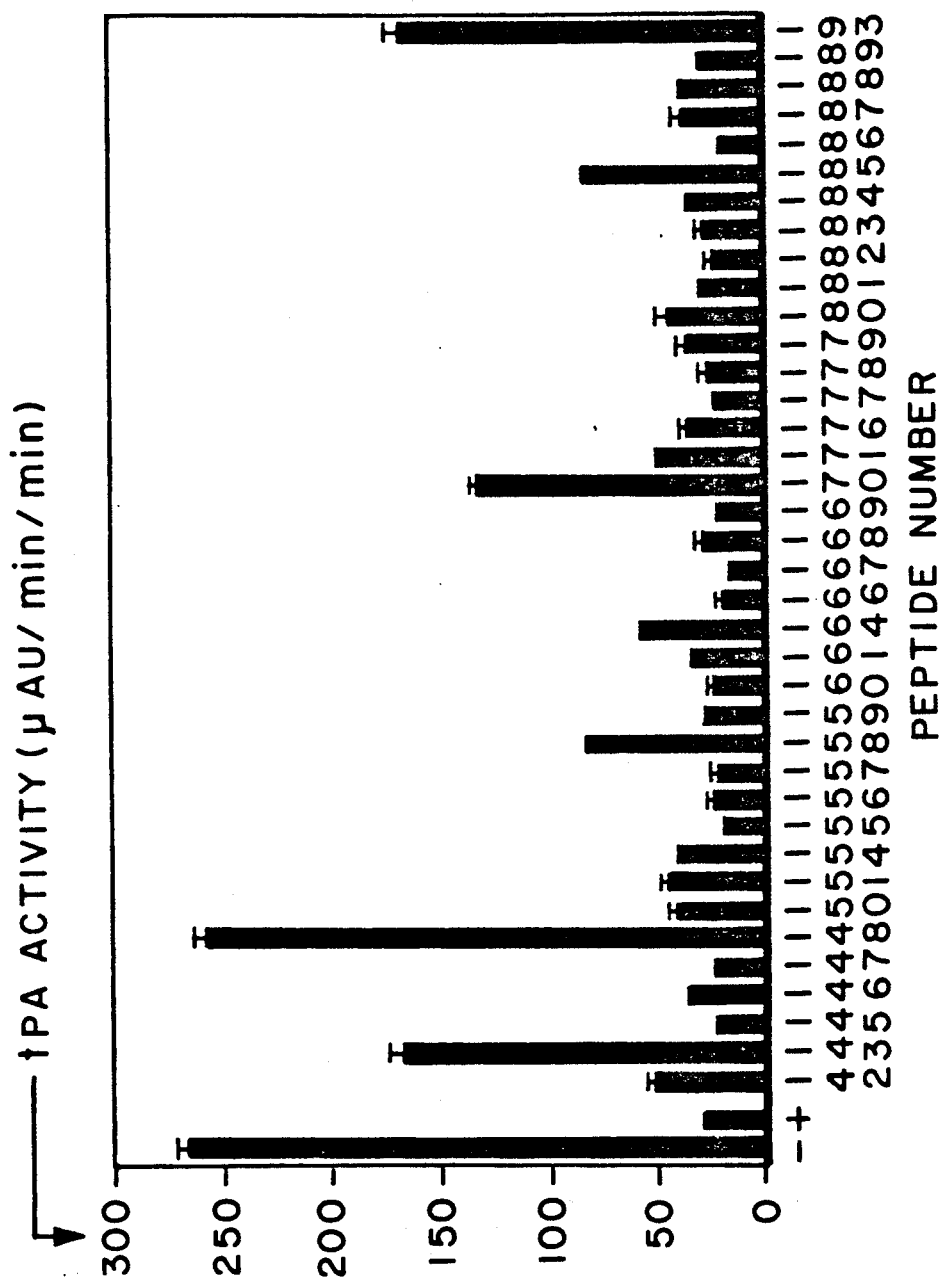

While the specification concludes with claims particularly pointing out and distinctly claiming the subject matter regarded as forming the present invention, it is believed that the invention will be better understood from the following detailed description taken in conjunction with the accompanying drawings in which:

FIG. 1 is a bar chart which shows the effect of various peptides (defined in Table 1, below) on the inactivation of tPA by PAI-1. The ability of the peptides to protect tPA from inactivation by PAI-1 was examined and the results are shown in FIG. 1. In each case, peptide and PAI-1 were first mixed, followed by the addition of tPA. Final concentrations were: 100 μg/ml peptide, 1.5 μg/ml PAI-1 and 50 ng/ml tPA in phospate buffered saline containing 0.01% sodium azide and 0.01% Tween 80%. After incubation for one hour at 37° C., samples were examined for remaining tPA enzymatic activity. The error bars represent the range of duplicate measurements of the tPA enzymatic activity in μAU/min/min.

Figure 2:
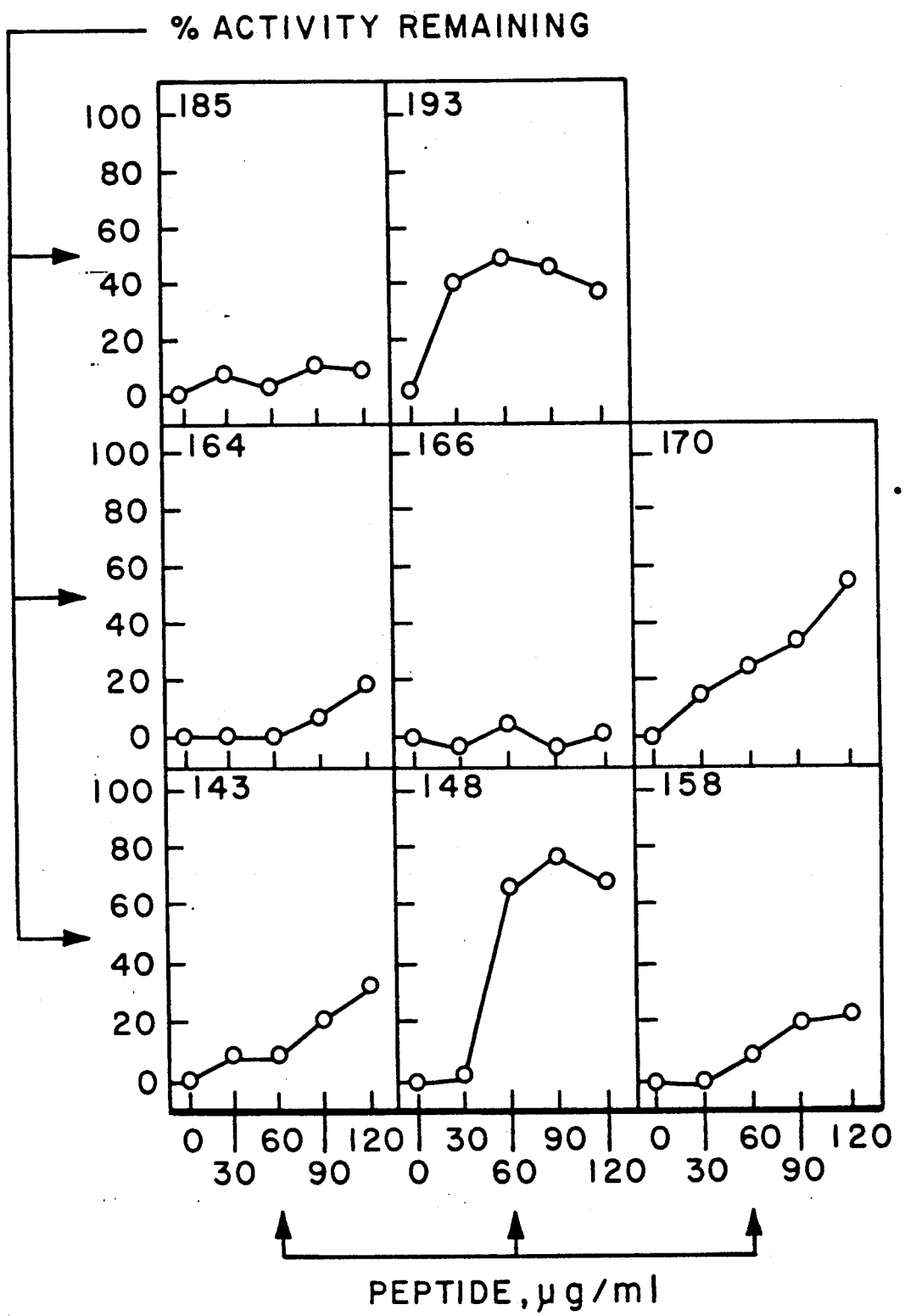

FIG. 2 is a graphical representation which shows the effect of peptide concentration on the maintenance of tPA activity in the presence of PAI-1 for eight peptides from FIG. 1. Peptides which appeared to protect tPA from inactivation by PAI-1, and one which did not (peptide 166), were examined at several concentrations (μg/ml) and results are shown in FIG. 2. Results are expressed as the percentage of tPA enzymatic activity remaining after incubation with tPA, PAI-1 and peptide relative to that seen with tPA alone. Peptide 166 was examined because of its apparent effect in inhibiting the binding of tPA to endothelial cells (see FIG. 3).

FIG. 3 is a bar chart which shows the effect of peptides on the binding of tPA to endothelial cells. Peptides from FIG. 1 were examined for their ability to inhibit the binding of [$^{125}$I]-tPA to human umbilical vein endothelial cells. Assays were performed as described under Materials and Methods, below, using a final peptide concentration of 15 μg/ml. All samples were assayed in duplicate. Bar height represents the result obtained for one duplicate point and the corresponding error bar represents the result obtained for the other. Results are shown in percent inhibition of binding.

Figure 4A:
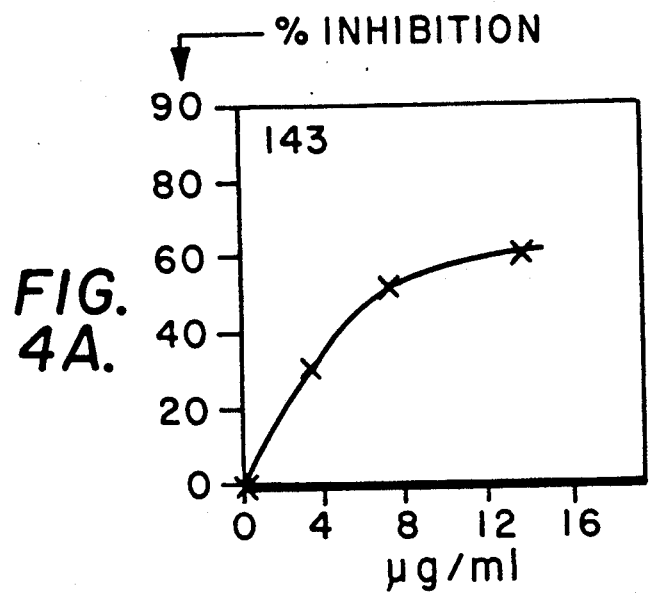
Figure 4B:
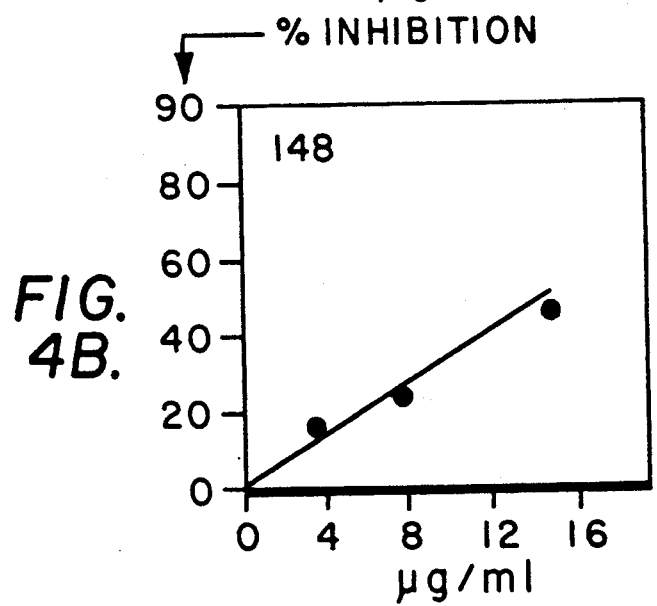
Figure 4C:
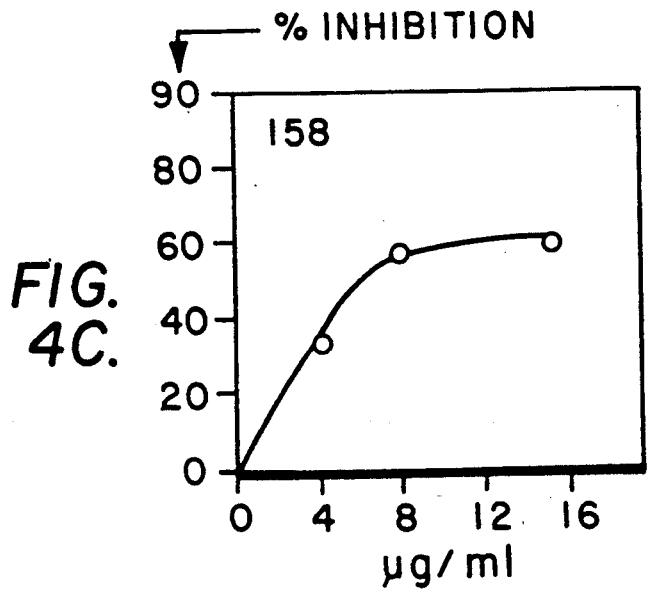

FIG. 4 is a graphical representation which shows the dose response curves for peptides 143, 148 and 158 of FIG. 3.

The effectiveness of tissue plasminogen activator in thrombolytic therapy is independent upon the rate at which therapeutically administered tPA reaches the clot site and the proportion of that tPA which is enzymatically active. Interactions between tPA and its main plasma inhibitor (PAI-1) and between tPA and the endothelial cells lining blood vessels are two factors which may limit efficacy. In an attempt to identify the regions of the tPA molecule involved in these interactions, a series of synthetic peptides with amino acid sequences corresponding to different regions of the native tPA molecule were examined for their ability to protect tPA from inactivation by PAI-1 and for their ability to reduce the binding of tPA to endothelial cells. Four peptides were identified which were especially effective at maintaining tPA activity in the presence of PAI-1 and two others were found which had a lesser effect. These same peptides unexpectedly were also found to inhibit the binding of tPA to endothelial cells. This suggests that the same regions of the tPA molecule are involved in both processes. None of the peptides inhibited the binding of tPA to fibrin.

The four most active of these inhibitory peptides were:
tPA(31-55),
tPA(81-105),
tPA(301-325) and
tPA(531-555).

The other two active inhibitor peptides were:
tPA(181-205) and
tPA(45-475).

The novel inhibitory peptides of this invention can be prepared by known solution and solid phase peptide synthesis methods.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group (BOC), various coupling reagents, e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCL in dioxane, boron tris-(trifluoracetate) and cyanogen bromide, and reaction in solution with isolation and purification of intermediates is well-known classical peptide methodology.

The preferred peptide synthesis method generally follows conventional Merrifield solid-phase procedures and modifications thereof. See Merrifield, *J. Amer. Chem. Soc.* 85, 2149-54 (1963) and *Science* 150, 178-85 (1965). This procedure, though using many of the same chemical reactions and blocking groups of classical peptide synthesis, provides a growing peptide chain anchored by its carboxy terminus to a solid support, usually cross-linked polystyrene, styrenedivinylbenzene copolymer or, preferably, p-methylbenzhydrylamine polymer for synthesizing peptide amides. This method conveniently simplifies the number of procedural manipulations since removal of the excess reagents at each step is effected simply by washing the polymer.

Further background information on the established solid-phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology* 32, pp. 221-296, F. F. Nold, Ed., Interscience Publishers, New York, 1969; and Erickson and Merrifield, *The Proteins*, Vol. 2, p. 255 et seq. (ed. Neurath and Hill), Academic Press, New York, 1976.

In a preferred modification of the conventional Merrifield solid-phase peptide synthesis as illustrated herein, the amino acid solid support resin is contained in polypropylene mesh packets such as described by Houghton, *Proc. Natl. Acad. Sci. USA* 82, 5131-5135 (1985). This enhanced procedure permits many different peptides to be sequenced simultaneously, by separating the solid support resin for different peptides in solvent permeable packets. The amino acid coupling can thereby be performed separately, while other steps, including deprotection, washing and neutralization, can be performed in a common reaction vessel.

Amino acids are shown herein either by standard one letter or three letter abbreviations as follows:

| Abbreviated Designation | | Amino Acid |
| --- | --- | --- |
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

In order to further illustrate the invention in greater detail, the following exemplary laboratory preparative work was carried out with the results as described and shown in Tables 1 and 2 and the accompanying FIGS. 1 to 4.

EXAMPLES

MATERIALS AND METHODS

Materials

A set of 38 peptides, each 25 amino acids in length, were prepared by the solid phase synthesis method as described by Houghton, *Proc. Natl. Acad. Sci. USA* 82, 5131-5135 (1985). These peptides (ID#142 to 193, Table 1) have sequences derived from the intact tPA amino acid sequence. PAI-1, single-chain melanoma tPA and glu-plasminogen were purchased from American Diagnostica, Inc. Human fibrinogen, plasmin substrate S-2251 (H-D-Val-Leu-Lys-p-nitroanilide-HCl) and fibrinogen fragment tPA stimulator were from Kabi Vitrum. Sodium [$^{125}$I]-iodide was purchased from Amersham Inc. and the bovine serum albumin (BSA) used in studies on the binding of [$^{125}$I]-tPA to endothelial cells was from Pentax Inc. Labile enzyme-free bovine gamma globulin was obtained from ICN Immunodiagnostics. Growth medium MCDB107 (MCDB105 plus 0.015 g/L glycine and 0.015 g/L potassium chloride) was purchased from Sigma Chemical Co. Endothelial cell growth supplement (ECGS) and human fibronectin (HFN) were from Collaborative Research. Fetal bovine serum (FBS) was from Hyclone Laboratories Inc. Plasticware, including 24-well culture plates, was from either Corning or Falcon Plastics. Except as otherwise noted, all other reagents were from Sigma or Fisher Chemical companies and were of the highest quality available.

tPA Enzyme Assays

An indirect amidolytic assay for tPA activity was performed by a conventional method as described by Ranby and Wallen, *Prog. Fibrinolytics* 5, 233–235 (1981) and Ranby, *Biochim. Biophys. Acta* 740, 461–469 (1982) but with the following modifications. The assay mixture contained 50 µg/ml human glu-plasminogen, 1 mM plasmin substrate S-2251, 130 µg/ml fibrinogen fragment stimulator, and 0 to 20 ng/ml tPA sample in phosphate-buffered saline containing 0.01% sodium azide and 0.01% Tween 80 (PBSAT) in a final volume of 100 µl. The assay was performed in a 96-well microtitration plate at room temperature. Reaction mixtures were overlaid with 50 µl mineral oil to prevent evaporation. Periodic readings were taken at 405 nm and referenced at 650 nm using a Molecular Devices Vmax plate reader. The first derivative of absorbance with respect to time was calculated and the slope of a plot of dA/dt vs time was proportional to tPA activity. Results were expressed in absorbance units ($\mu AU/min^2$) or as a percentage of control.

PAI-1 Inhibition Studies

The effect of peptides on the inactivation of tPA by PAI-1 was measured by incubating 1.5 µg/ml PAI-1, 30–120 µg/ml peptide and 50 ng/ml tPA in PBSAT. PAI-1 and peptide were first mixed, followed by the addition of tPA. After one hour at 37° C., residual tPA enzymatic activity was measured either immediately or after the samples had been frozen and stored.

Endothelial Cell Binding Assays

Assays examining the binding of [$^{125}$I]-tPA to endothelial cells were performed by a conventional method essentially as described by Hajjar et al., *J. Clin. Invest.* 80, 1712–1719 (1987), and Beebe, *Thromb. Res.* 46, 241–254 (1987). Briefly, cells were grown to confluence in 24-well dishes using MCDB107 growth medium supplemented with 180 µg/ml heparin, 30 µg/ml ECGS, 100 µg/ml gentamicin and 10% fetal bovine serum. Immediately prior to assay, plates were chilled to 4° C. and all wells were aspirated. Cells were washed 3 times with binding buffer (PBS, pH 7.2, 5.0 mg/ml BSA, 10 mM glucose, 0.01% Tween 80). Five hundred µl of buffer containing approximately 20 ng/ml of [$^{125}$I]-tPA and a test sample of peptide was then added. Incubations proceeded at 4° C. for 90 minutes. At the end of the incubation time, cells were washed rapidly 4 times with 500 µl aliquots of binding buffer. Cells were separated from the plates using 3% sodium dodecylsulfate (SDS) and the amount of radioactivity present was determined. Nonspecific binding was determined by carrying out incubations in the presence of an excess (2.0 µg/ml) of unlabeled tPA. Results obtained in the presence of the various peptides are expressed as a percentage of the specific binding obtained with no peptide present.

Fibrin Binding

Binding of tPA to fibrin was measured using the conventional method of Rijken et al., *J. Biol. Chem.* 257, 2920–2925 (1982). This method involves mixing thrombin with a solution containing tPA and fibrinogen, centrifuging the resulting clot and measuring the concentration of tPA antigen in the supernatant. In a final volume of 200 µl, the following were combined: 200 ng/ml single chain melanoma tPA, 200 µg/ml human fibrinogen, 15 µg/ml tPA peptide, 1.1 mg/ml bovine serum albumin, 0.55 mg/ml bovine gamma globulin and 10 mM ε-amino caproic acid in PBSAT. Controls omitted fibrinogen, peptide or both. Mixtures were clotted by the addition of 1 unit/ml bovine thrombin, incubated one hour at room temperature and centrifuged. tPA antigen in the supernatant was measured by conventional ELISA and the percentage bound calculated by difference using the antigen level of a control mixture with no fibrinogen as 0% bound. None of the peptides were found to influence the ELISA antigen determination at the level assayed.

Quantitation of tP Antigen Levels
A

An ELISA assay kit for tPA and PAI-1 was purchased from American Diagnostica Inc. and assays were performed according to printed protocols supplied by the manufacturer with the kit except that a single lot of melanoma tPA from American Diagnostica Inc. (product 111, lot 47-01) was used as the antigen standard throughout this work and 5.0 mg/ml of BSA and 2.5 mg/ml of bovine gamma globulin were included in ELISA buffers.

Labeling of tPA tPA was labeled using immobilized lactoperoxidase (enzymobeads, Bio-Rad) and following the printed protocol supplied by the manufacturer with the product. Briefly, 20–25 µg of tPA in 75 µof buffer (0.02M sodium phosphate, pH 7.2, 0.15M arginine chloride, 1% β-D-Glucose, 0.05% Tween 80) was mixed with 50 µl of the enzymobead reagent and 1.0 mCi of sodium [$^{125}$I]iodide. The reaction was allowed to proceed for 40 minutes at room temperature. Free $^{125}$I was then separated from tPA bound $^{125}$I by gel filtration on a Sephadex ® G-25 column. Electrophoretic analysis of the resulting product followed by silver staining revealed a single band migrating with a molecular weight indistinguishable from that of unlabeled tPA. Autoradiography indicated that all of the radioactivity present was associated with the band. The amount of tPA present was determined by ELISA assay on samples taken before and after labeling. Using this procedure, it was determined that greater than 95% of the tPA was recovered from the G-25 column. The specific activity of the [$^{125}$I]-tPA was approximately 0.5 µCi/pmol.

RESULTS

Effect of Peptides on the Inactivation of tPA by PAI-1 tPA was incubated with increasing concentrations of PAI-1 for one hour at 37° C. and the incubate was then assayed for residual tPA enzymatic activity. Based on these results, a ratio of tPA to PAI-1 was chosen at which approximately 90% of the enzymatic activity was inhibited and this rate was maintained in incubations performed in the presence of each of the peptides shown in Table 1. The first bar in FIG. 1 (marked "−") represents the enzymatic activity recovered when tPA alone was present in the incubation and the next bar (marked "+") shows the activity recovered when PAI-1 was present during the incubation. Each of the other bars represents the activity recovered when incubations were performed in the presence of tPA, PAI-1 and one of the 38 numbered peptides at a concentration of 100 μg/ml. Four peptides (143, 148, 170 and 193) were found to be especially effective at maintaining tPA activity, and two others (158 and 185) were active but with a lesser effect. When tPA and PAI-1 were preincubated prior to the addition of the tPA-protecting peptides, no recovery of activity was seen. This supports the inventors' belief that active peptides exert their effect by preventing the formation of the tPA-PAI-1 complex and not by either promoting the dissociation of the complex or by stimulating the activity of free enzyme.

The six active peptides and a marginally active peptide 164 were examined at several concentrations and the results are shown in FIG. 2. It can be seen that certain of the peptides (143, 158, 164 and 170) showed a steady, progressive increase in activity over the concentration range examined whereas the activity of others (148 and 193) rose dramatically and plateaued. In general, the results shown in FIG. 2 agree well with the results in FIG. 1. Exceptions are that peptide 143 had somewhat less activity in FIG. 2 than what would be expected from FIG. 1 results and peptide 185 showed essentially no activity. In the case of peptide 185, the freezing of incubation mixes prior to assaying for enzymatic activity appeared to cause a loss of the protective effect of the peptide (i.e. less tPA activity was recovered after a cycle of freezing and thawing). This suggests that the variable results obtained may be due to structural instability in either the peptide itself or in the complex formed by the peptide.

Effect of Peptides on the Binding of tPA to Endothelial Cells

The peptides shown in Table 1 were examined for their effect on the binding of tPA to cultured human umbilical vein endothelial cells. FIG. 3 shows the results obtained when peptides were assayed at a concentration of 15 μg/ml. The bars represent the percent inhibition of binding observed in the presence of peptide relative to that seen with no peptide present. Nonspecific binding was determined by performing assays in the presence of a 100-fold excess of unlabeled tPA and constituted approximately 30% of the total binding. All points were run in duplicate and nonspecific binding was subtracted in each case. The results indicate that the peptides 143, 148, 158, 170, 185 and 193, all of which inhibited the binding of tPA to PAI-1, also inhibited the binding of tPA to endothelial cells. Peptide 164 which had marginal activity in FIG. 1 also appeared to have marginal activity in FIG. 3. The results suggest that interactions between tPA and PAI-1 and interactions between tPA and endothelial cells are mediated by similar regions of the tPA molecule. As with the binding of tPA to PAI-1, FIG. 2, active peptides inhibited the binding of tPA to endothelial cells in a concentration dependent manner (e.g. the three dose response curves for peptides 143, 148 and 158 shown in FIG. 4).

Although the results obtained in the tests on tPA/PAI-1 binding are quite similar to those obtained for tPA/endothelial cell binding, there are some differences worth noting. First, adjacent peptides tend to be more similar in the effect they have on the binding of tPA to endothelial cells than on the effect they have on binding to PAI-1 (e.g. peptides adjacent to 143). Two of the peptides (143 and 158) appear to be more effective at inhibiting endothelial cell binding relative to the other active peptides than in inhibiting PAI-1 binding. Finally, peptide 166 was effective at inhibiting the binding of tPA to cells (FIG. 3) but had no effect on tPA/PAI-1 interaction (FIGS. 1 and 2). Therefore, even though similar regions of the tPA molecule may be participating in its binding to both PAI-1 and endothelial cells, the interactions involved are not identical. Differences probably stem, in part, from the fact that cell binding involves membrane-bound rather than free proteins; however, it is also possible that membrane proteins other than PAI-1 contribute to the binding of tPA to endothelial cells.

Effect of Peptides on the Binding of tPA to Fibrin

The therapeutic value of tPA stems largely from its ability to localize proteolytic activity to the immediate vicinity of the clot. Molecules which inhibited the binding of tPA to PAI-1 or to endothelial cells would be of little therapeutic value if they also inhibited the binding of tPA to fibrin. The peptides listed in Table 1 were examined for their effect on fibrin binding at a concentration of 15 μg/ml and results are shown in Table 2. It can be seen that none of the peptides examined, including those that were active in inhibiting the binding of tPA to endothelial cells at this concentration, were found to reduce the binding of tPA to fibrin.

TABLE 1

Sequences of Peptides Examined

| ID # | PEPTIDE NAME[a] | SEQUENCE |
| --- | --- | --- |
| 142 | tPA (21-45) | SPSQEIHARFRRGARSYQVICRDEK |
| 143 | tPA (31-55) | RRGARSYQVICRDEKTQMIYQQHQS |
| 145 | tPA (51-75) | QQHQSWLRPVLRSNRVEYCWCNSGR-amide |
| 146 | tPA (61-85) | LRSNRVEYCWCNSGRAQCHSVPVKS-amide |
| 147 | tPA (71-95) | CNSGRAQCHSVPVKSCSEPRCFNGG-amide |
| 148 | tPA (81-105) | VPVKSCSEPRCFNGGTCQQALYFSD-amide |
| 150 | tPA (101-125) | LYFSDFVCQCPEGFAGKCCEIDTRA |
| 151 | tPA (111-135) | PEGFAGKCCEIDTRATCYEDQGISY-amide |
| 154 | tPA (141-165) | TAESGAECTNWNSSALAQKPYSGRR-amide |
| 155 | tPA (151-175) | WNSSALAQKPYSGRRPDAIRLGLGN |
| 156 | tPA (161-185) | YSGRRPDAIRLGLGNHNYCRNPDRD-amide |
| 157 | tPA (171-195) | LGLGNHNYCRNPDRDSKPWCYVFKA-amide |
| 158 | tPA (181-205) | NPDRDSKPWCYVFKAGKYSSEFCST-amide |
| 159 | tPA (191-215) | YVFKAGKYSSEFCSTPACSEGNSDC-amide |
| 160 | tPA (201-225) | EFCSTPACSEGNSDCYFGNGSAYRG |
| 161 | tPA (211-235) | GNSDCYFGNGSAYRGTHSLTESGAS-amide |
| 164 | tPA (241-265) | SMILIGKVYTAQNPSAQALGLGKHN-amide |
| 166 | tPA (261-285) | LGKHNYCRNPDGDAKPWCHVLKNRR-amide |
| 167 | tPA (271-295) | DGDAKPWCHVLKNRRLTWEYCDVPS-amide |
| 168 | tPA (281-305) | LKNRRLTWEYCDVPSCSTCGLRQYS |
| 169 | tPA (291-315) | CDVPSCSTCGLRQYSQPQFRIKGGL-amide |

TABLE 1-continued

Sequences of Peptides Examined

| ID # | PEPTIDE NAME[a] | SEQUENCE |
|---|---|---|
| 170 | tPA (301–325) | LRQYSQPQFRIKGGLFADIASHPWQ-amide |
| 171 | tPA (311–335) | IKGGLFADIASHPWQAAIFAKHRRS-amide |
| 176 | tPA (361–385) | ERFPPHHLTVILGRTYRVVPGEEEQ-amide |
| 177 | tPA (371–395) | ILGRTYRVVPGEEEQKFEVEKYIVH-amide |
| 178 | tPA (381–405) | GEEEQKFEVEKYIVHKEFDDDTYDN-amide |
| 179 | tPA (391–415) | KYIVHKEFDDDTYDNDIALLQLKSD-amide |
| 180 | tPA (401–425) | DTYDNDIALLQLKSDSSRCAQESSV-amide |
| 181 | tPA (411–435) | QLKSDSSRCAQESSVVRTVCLPPAD-amide |
| 182 | tPA (421–445) | QESSVVRTVCLPPADLQLPDWTECE-amide |
| 183 | tPA (431–455) | LPPADLQLPDWTECELSGYGKHEAL-amide |
| 184 | tPA (441–465) | WTECELSGYGKHEALSPFYSERLKE-amide |
| 185 | tPA (451–475) | KHEALSPFYSERLKEAHVRLYPSSR-amide |
| 186 | tPA (461–485) | ERLKEAHVRLYPSSRCTSQHLLNRT-amide |
| 187 | tPA (471–495) | YPSSRCTSQHLLNRTVTDNMLCAGD-amide |
| 188 | tPA (481–505) | LLNRTVTDNMLCAGDTRSGGPQANL-amide |
| 189 | tPA (491–515) | LCAGDTRSGGPQANLHDACQGDSGG-amide |
| 193 | tPA (531–555) | ISWGLGCGQKDVPGVYTKVTNYLDW-amide |

[a]Numbering includes the putative signal peptide and prosequences described by Ny et al. (17). The serine found at the N-terminus of the mature protein is residue 36 using this numbering scheme.

TABLE 2

Effect of tPA Peptides on Binding of tPA to Fibrin.[a]

| Peptide | % Bound | Peptide | % Bound |
|---|---|---|---|
| None | 48 | 168 | 54 |
| 142 | 58 | 169 | 55 |
| 143 | 57 | 170 | 51 |
| 145 | 56 | 171 | 51 |
| 146 | 54 | 176 | 53 |
| 147 | 55 | 177 | 51 |
| 148 | 50 | 178 | 50 |
| 150 | 52 | 179 | 54 |
| 151 | 53 | 180 | 49 |
| 154 | 56 | 181 | 49 |
| 155 | 54 | 182 | 52 |
| 156 | 52 | 183 | 53 |
| 157 | 54 | 184 | 51 |
| 158 | 53 | 185 | 49 |
| 159 | 54 | 186 | 50 |
| 160 | 56 | 187 | 51 |
| 161 | 57 | 188 | 52 |
| 164 | 53 | 189 | 50 |
| 166 | 57 | 193 | 48 |
| 167 | 50 | | |

[a]See above for conditions.

Various other examples will be apparent to the person skilled in the art after reading the present disclosure without departing from the spirit and scope of the invention. It is intended that all such other examples be included within the scope of the appended claims.

What is claimed is:

1. A peptide or peptide amide having inhibitory activity against inactivation of tPA by PAI-1 and inhibitory activity against the binding of tPA to human endothelial cells and an amino acid sequence substantially identical to that of a native tPA fragment selected from the group consisting of:

Arg Arg Gly Ala Arg Ser Tyr Gln Val Ile Cys Arg Asp Glu Lys Thr Gln Met Ile Tyr Gln Gln His Gln Ser,

Val Pro Val Lys Ser Cys Ser Glu Pro Arg Cys Phe Asn Gly Cly Thr Cys Gln Gln Ala Leu Tyr Phe Ser Asp,

Asn Pro Asp Arg Arp Ser Lys Pro Trp Cys Tyr Val Phe Lys Ala Gly Lys Tyr Ser Ser Glu Phe Cys Ser Thr,

Leu Arg Gln Tyr Sr Gln Pro Gln Phe Arg Ile Lys Gly Gly Leu Phe Ala Asp Ile Ala Ser His Pro Trp Gln,

Lys His GLu Ala Leu Ser Pro Phe Tyr Ser Glu Arg Leu Lys Glu Ala His Val Arg Leu Tyr Pro Ser Ser Ar, and Ile Ser Trp Gly Leu Gly Cys Gly Gln Lys Asp Val Pro Gly Val Tyr Thr Lys Val Thr Asn Tyr Leu Asp Trp.

* * * * *

UNITED STATES PATENT AND TRADEMARK OFFICE
CERTIFICATE OF CORRECTION

PATENT NO. : 5,039,791

DATED : Aug. 13, 1991

INVENTOR(S) : Arthur J. Wittwer  et al

It is certified that error appears in the above-identified patent and that said Letters Patent is hereby corrected as shown below:

At col. 6, line 21, "tP" should read --tPA--.

At col. 6, line 22, cancel "A".

At col. 10, line 35, "Cly" should read --Gly--.

At col. 10, line 36, "Arp" should read --Asp--.

At col. 10, line 39, "Sr" should read --Ser--.

Signed and Sealed this

Eighth Day of September, 1992

Attest:

DOUGLAS B. COMER

*Attesting Officer*  *Acting Commissioner of Patents and Trademarks*